US012586693B2

(12) United States Patent
Al Ahmad et al.

(10) Patent No.: US 12,586,693 B2
(45) Date of Patent: Mar. 24, 2026

(54) ELECTRICAL COMPONENT COMPRISING DATE FRUIT DERIVED MELANIN

(71) Applicant: United Arab Emirates University, Al Ain (AE)

(72) Inventors: Mahmoud F.Y. Al Ahmad, Al Ain (AE); Afaf Kamal Eldin, Al Ain (AE); Muneeba Alam, Al Ain (AE)

(73) Assignee: United Arab Emirates University (AE)

( * ) Notice: Subject to any disclaimer, the term of this patent is extended or adjusted under 35 U.S.C. 154(b) by 0 days.

(21) Appl. No.: 18/197,191

(22) Filed: May 15, 2023

(65) Prior Publication Data
US 2024/0383907 A1 Nov. 21, 2024

(51) Int. Cl.
| | |
|---|---|
| *H01B 1/12* | (2006.01) |
| *C07D 487/06* | (2006.01) |
| *G01N 27/22* | (2006.01) |
| *H10K 30/50* | (2023.01) |
| *H10K 85/60* | (2023.01) |

(52) U.S. Cl.
CPC ........... *H01B 1/124* (2013.01); *C07D 487/06* (2013.01); *G01N 27/223* (2013.01); *G01N 27/226* (2013.01); *H01B 1/12* (2013.01); *H10K 30/50* (2023.02); *H10K 85/6572* (2023.02)

(58) Field of Classification Search
CPC .... C09B 69/104; G01N 27/226; H01B 1/124; H10K 85/6572; H10K 30/50
See application file for complete search history.

(56) References Cited

U.S. PATENT DOCUMENTS

| | | | | |
|---|---|---|---|---|
| 5,958,500 A | * | 9/1999 | Silver | C13B 10/00 |
| | | | | 426/622 |
| 2009/0107217 A1 | * | 4/2009 | Huang | G01N 29/4427 |
| | | | | 73/61.79 |
| 2018/0200321 A1 | * | 7/2018 | Abdelhadi | A61K 9/10 |
| 2021/0013567 A1 | * | 1/2021 | Solis Herrera | H01M 4/60 |

FOREIGN PATENT DOCUMENTS

| | | | | | |
|---|---|---|---|---|---|
| CH | 715443 A2 | * | 4/2020 | | A23L 33/105 |
| CN | 111171596 A | * | 5/2020 | | |

(Continued)

OTHER PUBLICATIONS

Alam, M.Z., Ramachandran, T., Antony, A. et al. Melanin is a plenteous bioactive phenolic compound in date fruits (*Phoenix dactylifera* L.). Sci Rep 12, 6614 (Apr. 2022). https://doi.org/10.1038/s41598-022-10546-9 (Year: 2022).*

(Continued)

*Primary Examiner* — Monique R Jackson
(74) *Attorney, Agent, or Firm* — Boyle Fredrickson, S.C.

(57) ABSTRACT

A process of extracting date fruit melanin from the date fruit for use in electrical application comprising providing a date fruit puree, mixing the puree with an alkaline solution to solubilize melanin, followed by acid precipitation of melanin using an inorganic acid. The melanin obtained finds its use as an electrically conductive portion in an electronic component of devices comprising of a sensor, a photovoltaic cell and/or bioelectronic device.

11 Claims, 8 Drawing Sheets
(8 of 8 Drawing Sheet(s) Filed in Color)

(56) References Cited

FOREIGN PATENT DOCUMENTS

WO      2003030194  A1      4/2003
WO      2018009032  A1      1/2018

OTHER PUBLICATIONS

Machine translation of CN111171596A, published May 2020, Powered by EPO and Google. (Year: 2020).*

Pradhan et al, Nature-derived materials for the fabrication of functional biodevices, 2020, Materials Today Bio 7, 100065, pp. 1-24 (Year: 2020).*

Wu et al, Synthesis of water-soluble dopamine-melanin for ultrasensitive and ultrafast humidity sensor, 2016, Sensors and Actuators B 224, pp. 178-184. (Year: 2016).*

Sava et al., A novel melanin-like pigment derived from black tea leaves with immuno-stimulating activity, 2001, Food Research International 34, pp. 337-343. (Year: 2001).*

Sava et al., Isolation and characterization of melanic pigments derived from tea and tea polyphenols, 2001, Food Chemistry 73, pp. 177-184. (Year: 2001).*

Alam et al, Inability of total antioxidant activity assays to accurately assess the phenolic compounds of date palm fruit (*Phoenix dactylifera* L.), 2021, NFS Journal 22, pp. 32-40. (Year: 2021).*

Machine translation of CH715443A2, published Apr. 2020, Powered by EPO and Google. (Year: 2020).*

Baliga, A review of the chemistry and pharmacology of the date fruits (*Phoenix dactylifera* L.), 2011, Food Research International 44, pp. 1812-1822. (Year: 2011).*

Hammouda, Detailed Polyphenol and Tannin Composition and Its Variability in Tunisian Dates (*Phoenix dactylifera* L.) at Different Maturity Stages, 2013, Journal of Agricultural and Food Chemistry 61, pp. 3252-3263. (Year: 2013).*

Ligonzo, Electrical and optical properties of natural and synthetic melanin biopolymer, 2009, Journal of Non-Crystalline Solids 355, pp. 1221-1226. (Year: 2009).*

Kurian, Noble K., "Extraction and Purification of Melanin From Various Cells and Tissues", Department of Microbiology, Atmiya University, Rajkot (May 27, 2022).

* cited by examiner

ELECTRICAL COMPONENT COMPRISING DATE FRUIT DERIVED MELANIN

FIELD OF INVENTION

The invention is related to the field of electrically conductive materials. More specifically, the invention relates to using Date fruit derived melanin as an electrically conductive material in electronic devices such as humidity sensors and photovoltaic cells.

BACKGROUND OF THE INVENTION

Melanin is a prevalent polymer responsible for the pigmentation in many lifeforms. Melanin as a compound in general is quite complex and is structurally diverse. Due to their stable free radical state, ultraviolet-visible (UV-Vis) light absorption, complexation and ion-exchange properties, charge storage and high conductivity, melanin is attracting attention in numerous applications in the electrical, biomedical and technology fields.

However, melanin obtained from natural sources are insoluble in nature, which limits its usage in many electrical, optical and biological applications.

There is a need to find new sources of melanin which are easily available and the extraction process is simpler. Also, the melanin extracted needs to be sufficiently soluble while retaining its electrical and conductive properties.

SUMMARY OF THE INVENTION

The applicant has developed a new method of extracting melanin from date fruit. The method involves alkaline extraction of melanin following by acid precipitation using an inorganic acid. The melanin extracted by this method has high conductivity, high electron mobility and material permittivity. Owing to these characteristics, the melanin extracted finds is use as part of electrical component of electrical devices such as sensors, solar cell, batters to name a few.

According to one aspect of the invention, there is provided a process of extracting date fruit melanin from date fruit for use in electrical applications comprising providing date fruit puree; and
  alkaline extraction of crude melanin.

The process further comprises deseeding and grinding the date fruit to form the date fruit puree. The grinding of the date fruit is preferably performed in absence of water. However, in an alternate embodiment, water may be added to the date fruit prior to or while grinding.

The step of alkaline extraction of crude melanin comprises mixing the date fruit puree with sodium hydroxide. Melanin is soluble in an alkaline solution. Upon mixing, the melanin from the date fruit puree is solubilized into the alkaline solution.

The sodium hydroxide solution is preferably maintained at 2 Molar.

The method further comprises centrifuging the alkaline solution and separating the supernatant from the precipitate. The supernatant comprises crude melanin.

The method further comprising precipitating the crude melanin by mixing the supernatant with an inorganic acid. The inorganic acid may be selected from hydrochloric acid, sulphuric acid and nitric acid. In a preferred embodiment, hydrochloric acid is used for precipitating the crude melanin.

The method further comprises forming an electrical component comprising an electrically conductive portion that comprises the date fruit melanin extracted from the aforementioned process to form the electrically conductive portion.

According to another aspect of the invention, there is provided an electronic component comprising an electrically conductive portion comprising of one or more electrodes and a date fruit derived melanin polymer. The date fruit derived melanin is placed in connection with the one or more electrodes. 16. The date fruit derived melanin polymer may be in further connection with an inorganic material. Further, the electrodes comprise gold.

The date fruit derived melanin may be used as dry polymer or as an aqueous or gel suspension of the polymer.

The conductivity of date fruit derived melanin ranges from about 0.14 siemens per meter to 119.86 siemens per meter.

The electron mobility of date fruit derived melanin ranges from about 0.15 to about 72.39.

The material permittivity of date fruit derived melanin ranges from about 132 to 7330.

In embodiments, the electronic device comprises any one of: a sensor, a photovoltaic cell, and/or bioelectronic component. In a preferred embodiment, the electronic device is humidity sensor device or a photovoltaic cell.

According to another aspect of the invention, there is provided a method of measuring humidity using a humidity sensor device comprising a date fruit derived melanin polymer in connection with one or more electrodes. The method comprises of applying a voltage across the electrodes, measuring a current generated in the circuit, and obtaining a current humidity level.

The method further comprises of generating a library of results for humidity measurement. The results are provided as table consisting of a column indicating the current generated against a corresponding humidity measurement in the corresponding column. These measurements are provided over a range of different humidity levels.

The method further comprises comparing the current generated to the corresponding humidity measurement result in the library, wherein the corresponding humidity measurement result is the current humidity level.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Further features of the invention are described hereinafter by way of a non-limiting example of the invention, with reference to and as illustrated in the accompanying diagrammatic drawing. In the drawings:

FIG. 2a shows graph of Direct current IV measurement and CV profiling for an applied frequency of 1 Hz measured under light conditions; FIG. 2b shows current-time measurements with dark and light cycling extracted from Cyclic Voltammetry applied with voltage range −500 mV to 500 mV; FIG. 2c shows current versus time data at two voltages, 3 V and −3 V, and in dark and light conditions; FIG. 2d shows current-time measurements with light cycling extracted from Cyclic Voltammetry measured again after 12 days with applied voltage −500 mV to 500 mV;

FIG. 4a shows IV characterization at two different dilutions and with pure water as a control, measured under light conditions; FIG. 4b shows capacitance-voltage profiling at two different dilutions and with pure water as a control, measured under light conditions; FIG. 4c shows current-time measurements for maximum dilution with dark and light cycling extracted from Cyclic Voltammetry; FIG. 4d shows capacitance versus time data for measurements with an applied frequency of 10 Hz at two voltages 3 V and −3 V and in dark and light conditions. $D_{min}$ and $D_{max}$ are the maximum and minimum concentration respectively.

FIG. 5a shows IV characterization of DM melanin suspension and SM melanin performed in dark (DMD and SMD respectively) and light conditions (DM and SM respectively) with an applied frequency of 10 Hz. FIG. 5b shows capacitance-voltage profiling of DM melanin suspension and SM melanin suspension measured in dark and light conditions with 10 Hz frequency applied.

DETAILED DESCRIPTION OF THE DRAWINGS

The invention relates to a method of extracting melanin from date fruit. The melanin extracted from the date fruit is referred to as Date fruit derived Melanin or Date Melanin (DM).

Although there are a variety of sources for melanin, in the Middle East region, date palms are available abundantly. Date palms are heat and drought resistant perennial crops and can easily grow and fruit in the desert regions of the Middle East and Northern Africa. The inventors have found a new method to extract melanin from the local resources. As the date fruit is used in the manufacturing of melanin, there is no adverse effect on the plant and the same tree may be used for continuous production of date fruit, which in turn provides for a continuous supply of raw material for production of melanin. In contrast, other melanin extraction methods permanently destroy the source plant.

The melanin in general obtained from the plant or natural sources are insoluble in nature. Melanin in nature is attached to a protein moiety. During alkali extraction in general, the protein moiety is cleaved from the melanin portion making melanin insoluble in most organic solvents, acids and water.

The inventors have advantageously developed a method of extracting melanin which includes alkali extraction of the melanin from the date fruit puree followed by acid precipitation. The melanin isolated from such technique can be purified by mixing in organic solvents. The organic solvents do not solubilize melanin, however, they aid in the removal of any lipid or fibre remaining from the alkaline extraction and acid precipitation steps.

The melanin extracted using the method of the invention has been advantageously found to have higher conductivity and therefore has a huge potential for its use as part of the electrode system in an electronic circuit/device.

Method of Extracting Date Melanin or Date Fruit Derived Melanin (DM)

Figure 1:
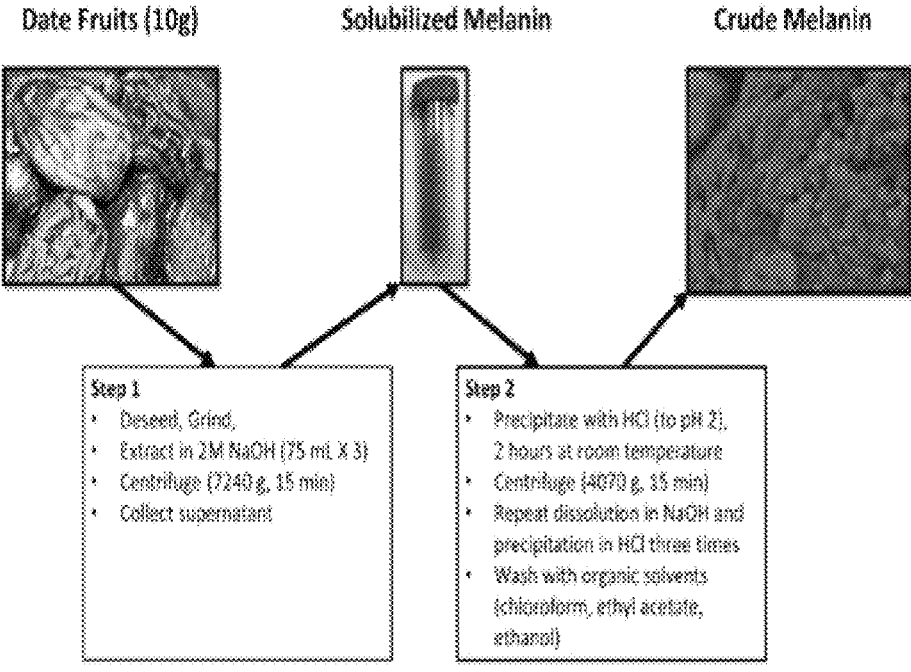
FIG. 1 shows a procedure for extraction of date fruit melanin (DM) in accordance with the invention.

FIG. 1 illustrates a method of extracting DM from date fruits in accordance with the invention. Date melanin (DM) was extracted from date fruits belonging to the genus *Phoenix dactylifera*, L. The process of extracting DM involves alkaline extraction of melanin, followed by precipitation using an inorganic acid.

In general, the process involves deseeding the date fruit followed by grinding the deseeded fruit to form a date fruit puree. Crude melanin is extracted from the puree using an alkaline solution. Upon mixing the puree with the alkaline solution, the suspension is centrifuged. Melanin is soluble in the alkaline solution and upon centrifugation, can be obtained from collecting the liquid portion "supernatant". The precipitate formed contains fruit fibres and other organic resides from the fruit puree.

In one example, the process involves deseeding 10 grams of whole date fruit. The deseeded fruit is then grinded by using any conventional techniques in the art, to form a date fruit puree. The puree is mixed or homogenised in 75 ml of 2Molar Sodium hydroxide solution by Ultra-Turrax homogenization for 30 minutes. The homogenization process or mixing is carried out with intermittent centrifugation at a relative centrifugation force of 7240 Xg for 15 min at room temperature.

On centrifugation it is observed that the supernatant contains solubilized crude melanin and is separated from the precipitate. Owing to the presence of melanin in the supernatant, the supernatant is dark brown in color.

For precipitating the melanin, the supernatant is treated or mixed with concentrated hydrochloric acid at pH 2 and allowed to rest for 2 hours. The mixture is then centrifuged at a relative centrifugation force of 4070 Xg for 15 min at room temperature to precipitate the melanin.

To increase the purity of the melanin, the process of solubilizing melanin in sodium hydroxide followed by precipitation with concentrated hydrochloric acid is repeated to obtain a more concentrated melanin in precipitate. The step of solubilizing melanin and precipitating with hydrochloric acid is repeated about three times.

The crude melanin precipitate is optionally washed using organic solvents such as chloroform, ethyl acetate, and ethanol to remove lipids and other residues remaining from the date fruit puree.

The crude melanin obtained from the above process was investigated for electrical and conductive properties in accordance with the invention.

Characterization of the Melanin The characterization of the melanin obtained from the above process was done using a Gamry reference 3000 equipment. For comparison purpose, *Sepia officinalis* melanin (SM) was purchased from Sigma Chemical Company (St. Louis, Missouri, USA) and was used without further purification.

Three sets of experiments were conducted. The first set was conducted using the dry DM. Second set of experiment was conducted using a suspension of DM in water or an aqueous suspension of DM. the third set of experiment was conducted using to compare the DM and SM suspension in water and in Dimethyl sulfoxide (DMSO).

The experiments were conducted using a Gamry reference 3000 equipment. The Gamry reference 3000 is capable of performing cyclic Voltammetry, electrochemical impedance (EIS) and capacitance-voltage (CV), and IV measurements.

To perform the experiments, the melanin samples were loaded into coaxial adaptors, which were attached to the cables of the Gamry Reference. Several electrical measurements were taken including; current-voltage (IV), current-time, capacitance-time, capacitance-voltage (CV), cyclic voltammetry and capacitance-frequency profiles.

The voltages varied over three ranges; −250 mV to 250 mV, −300 mV to 300 mV, and −500 mV to 500 mV. The experiments were conducted for between 180 to 600 seconds and during the experiments the frequencies between 1 Hz and 100 kHz were used. The optical conditions were varied by performing measurements in the dark and under ambient light conditions. All experiments were conducted at room temperature.

IV and CV measurements were used for extracting the electrical properties of the DM and SM melanin.

Cyclic voltammetry measures the current that is generated in an analyte when a voltage is applied in excess of that predicted by the Nernst equation. It is performed by linearly ramping the potential of a working electrode versus time in cyclical phases and measuring the resulting current. The voltage is measured between a reference electrode and the working electrode and the current is measured between a counter electrode and the working electrode. Cyclic voltammetry gives insight into reduction and oxidation processes of an analyte as well as the electron-transfer initiated chemical reactions.

EIS is obtained by measuring the current generated when an AC potential is applied to an electrochemical cell. It is typically measured with a small excitation signal to maintain a pseudo-linear response, that is, for a sinusoidal applied potential, a sinusoidal current is generated at the same frequency but with a phase shift. The measurements are usually performed in steady state conditions to avoid drift errors. With CV and IV measurement, an applied voltage is varied and the capacitance and current are measured respectively.

With Cyclic voltammetry, the Gamry reference it can apply scan rates from 1 mV/s to 1000 V/s. It allows for specification of the initial potential, first scan limit, second scan limit, final potential as well as step size. Both single and multiple cycle cyclic voltammetry can be specified. The device is used with Physical Electrochemistry Software. For EIS, the Gamry reference can perform measurements within the frequency range 10 µHz-1 MHz and up to maximum 3V ac voltage amplitude and 3 A ac current amplitude. It can measure impedances in the range of 1 mΩ to $10^{13}$Ω. Potentiostatic EIS was used as the test identifier. The number of points per decade as well as the area are also specified. With Echem Analyst, data can be analysed using Bode and Nyquist plots. The device is used with Electrochemical Impedance Spectroscopy Software. Lastly for the CV and IV measurements, the instrument can apply a maximum potential of up to +/−32V for current values of +/−1.5 A or potential of +/−15V for current values in the range +/−3 A. The system has an applied and measured accuracy of potential ±1 mV±0.2% of the value of the setting and an applied and measured resolution of current of ±0.2% of values between 3 A and 3 nA.

Electrical Parameter Extraction Method

The measurements IV and CV measurements were conducted in order to extract several parameters. The leakage current $I_0$, conductivity σ, voltage coefficients k and γ, were extracted by curve fitting the IV measurements to the polynomial function given in equation (1). The ideality factor n was calculated by fitting the measurements to the exponential function given in (2) and subsequently the mobility µ was calculated using equation (3)[18], $$I = I_0 + \sigma V + kV^2 + \gamma V^2 \qquad (1)$$

$$I = I_s e^{\frac{qV}{nKT}} \qquad (2)$$

$$\mu = \frac{\sigma}{nq} \qquad (3)$$

Where $I_s$ is the saturation current, q is the electron charge, K is the Boltzmann constant and T is room temperature in kelvin. The doping concentration $N_D$, and dielectric constant between the electrodes $\varepsilon_s$ were extracted from the linear part of the slope of the plot of $1/C^2$ verses voltage, using equations (4) to (6).

$$N_D = 2 \Big/ \left( q\varepsilon_s A_C^2 \left( \frac{\Delta\left(1/C^2\right)}{\Delta V} \right) \right) \qquad (4)$$

$$C_C = 2\pi\varepsilon_e\varepsilon_0 l / \ln(b/a) \qquad (5)$$

$$\varepsilon_s = \varepsilon_e\epsilon_0 \qquad (6)$$

where AC is the capacitor area (94.2478 mm$^2$), CC is the coaxial cable capacitance ε0 is the vacuum permittivity, $\varepsilon_\theta$ is the effective permittivity of the media, I is the cable length and b is the inner radius of the outer conductor and a is the outer radius of the inner conductor respectively.

To obtain the relative permittivity, the ratio of capacitance measured with melanin in the coaxial adaptor to the capacitance measured with water in the coaxial adaptor, was multiplied by the dielectric constant of water. This can be seen from equation (5). The Debye Length $L_D$, was calculated using equation (7).

$$L_D = \sqrt{\varepsilon_s KT/q^2 N} \qquad (7)$$

Results from Dry DM Melanin Characterization

FIGS. 2*a*-2*d* show graph providing the characterization results of dry DM.

Figures 2A, 2B, 2C, 2D:
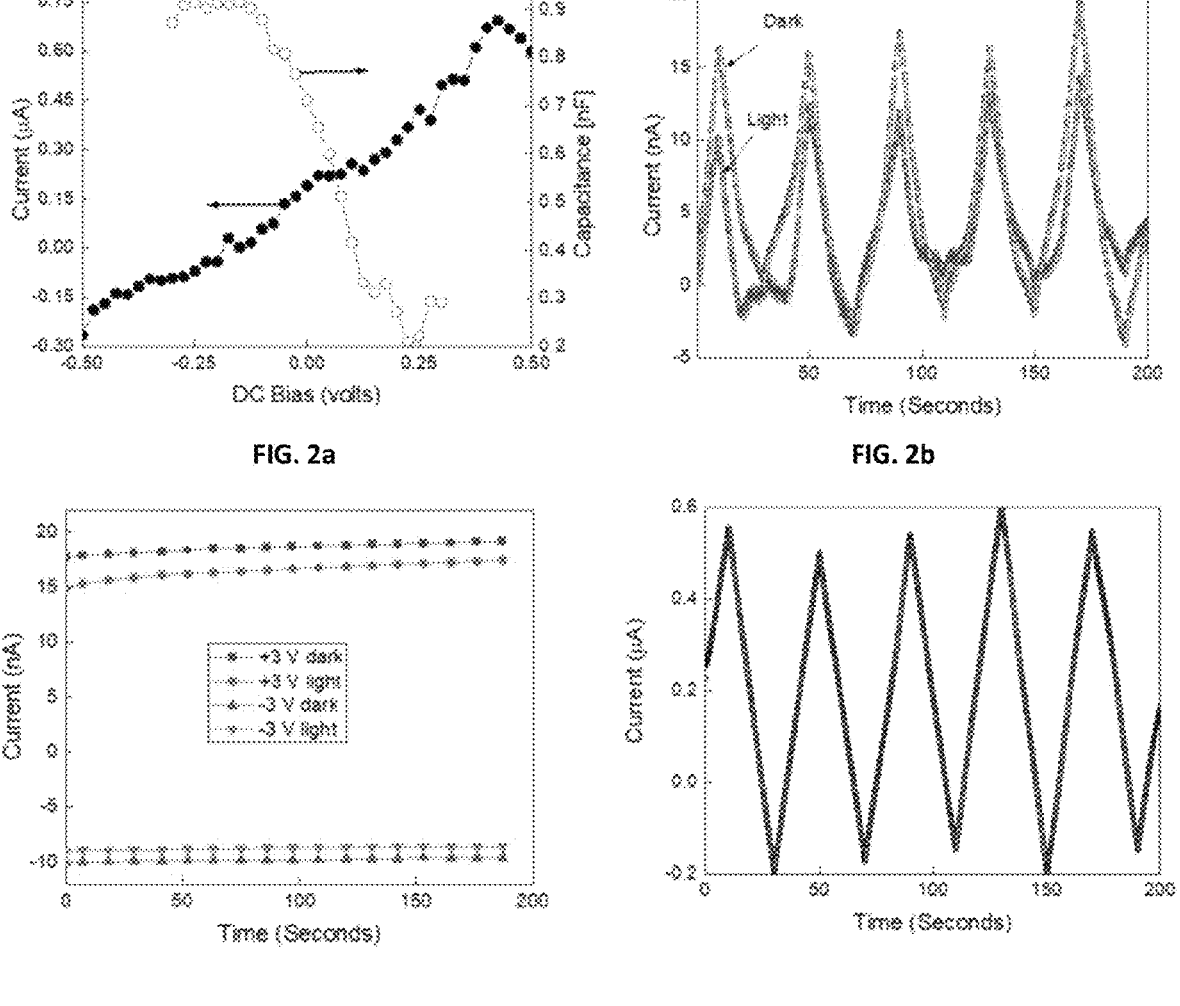
FIGS. 2a-2d shows graphs providing the characterization of dry DM.

In FIG. 2*a*, the direct current IV measurements (indicated in the graph as dark circles) are shown. As the applied voltage is low, the IV dependence follows Ohms law. Also, the CV curve (indicated in the graph as unfilled circles) is shown for an applied frequency of 1 Hz. It exhibits an exponential decay curve, which is characteristic of semiconductor behaviour.

FIG. 2*b* illustrates the results of cyclic voltammetry performed on the dry DM with a voltage applied in the range of −500 mV to 500 mV. The plots for the current versus time were extracted for measurements conducted when the melanin was held in the dark and when the melanin was illuminated by light. The current peaks for the dark cycling and higher than the current peaks achieved with light cycling, with maximums of about 20 nA and 14.5 nA respectively.

FIG. 2c illustrates the current variation verses time performed on dry DM. The experiments were conducted in both dark and light conditions. In general, the current measured at higher applied voltage (3 V) was greater than the current measured at the lower applied voltage (−3 V). For the lower applied voltage, the measurements done under light conditions indicated higher current. The reverse is true for the higher applied voltage, since the measurements in the dark conditions gave a higher current than those done under light conditions. The results further indicate that there may be a cutoff voltage, across which the relationships may switch.

The samples used for the light cycling experiment shown in FIG. 2b was measured again by Cyclic voltammetry after 12 days. The current versus time plots are shown in FIG. 2d. The maximum amplitude is seen to be significantly higher (over 38 times higher), with a maximum of about 0.6 μA.

Results from Characterization of DM in Suspension

For the characterization of DM in suspension, two different concentrations of the DM suspension were considered: a) $d_{min}$=0.3 mg/mL and b) $d_{max}$=30 mg/mL. The suspensions were prepared in water. Pure water was used as control. The same volumes were used for all experiments.

Figure 3A:
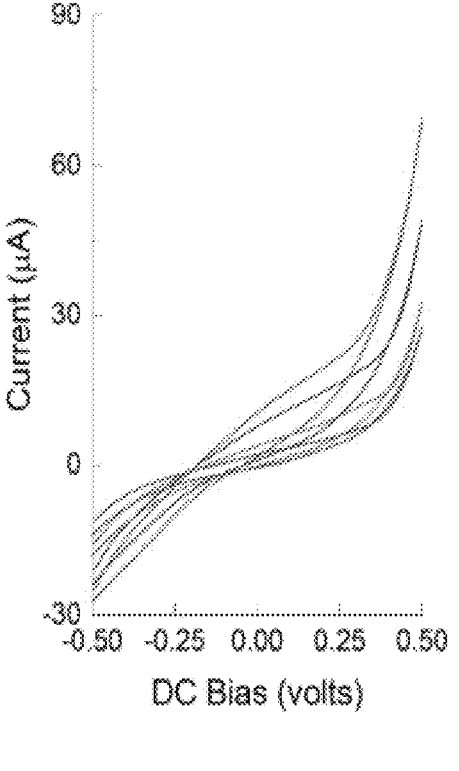
FIG. 3a shows graphs of cyclic voltammetry for DM melanin suspension for maximum dilution with light cycling over the voltage range −0.5V to 0.5V.
Figure 3B:
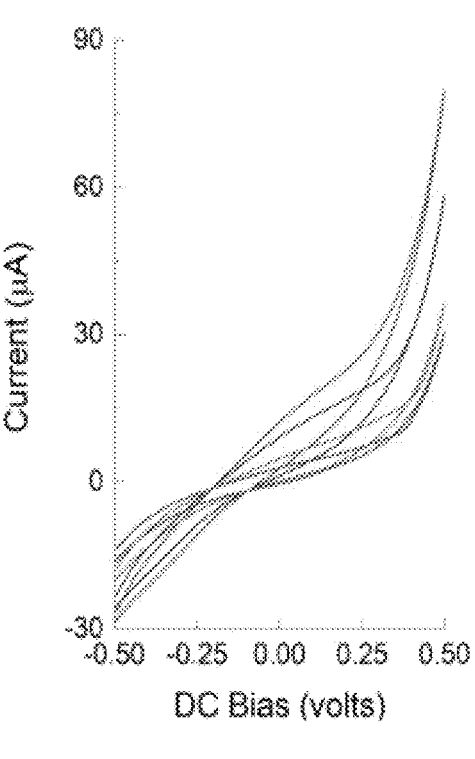
FIG. 3b shows graphs of cyclic voltammetry for DM melanin suspension for maximum dilution with dark cycling over the voltage range −0.5V to 0.5V.

The cyclic voltammogram for maximum dilution with light cycling is shown in FIG. 3a and with dark cycling is shown in FIG. 3b. The graphs show similar performance; however, the dark measurements exhibit higher current values.

Figures 4A, 4B, 4C, 4D:
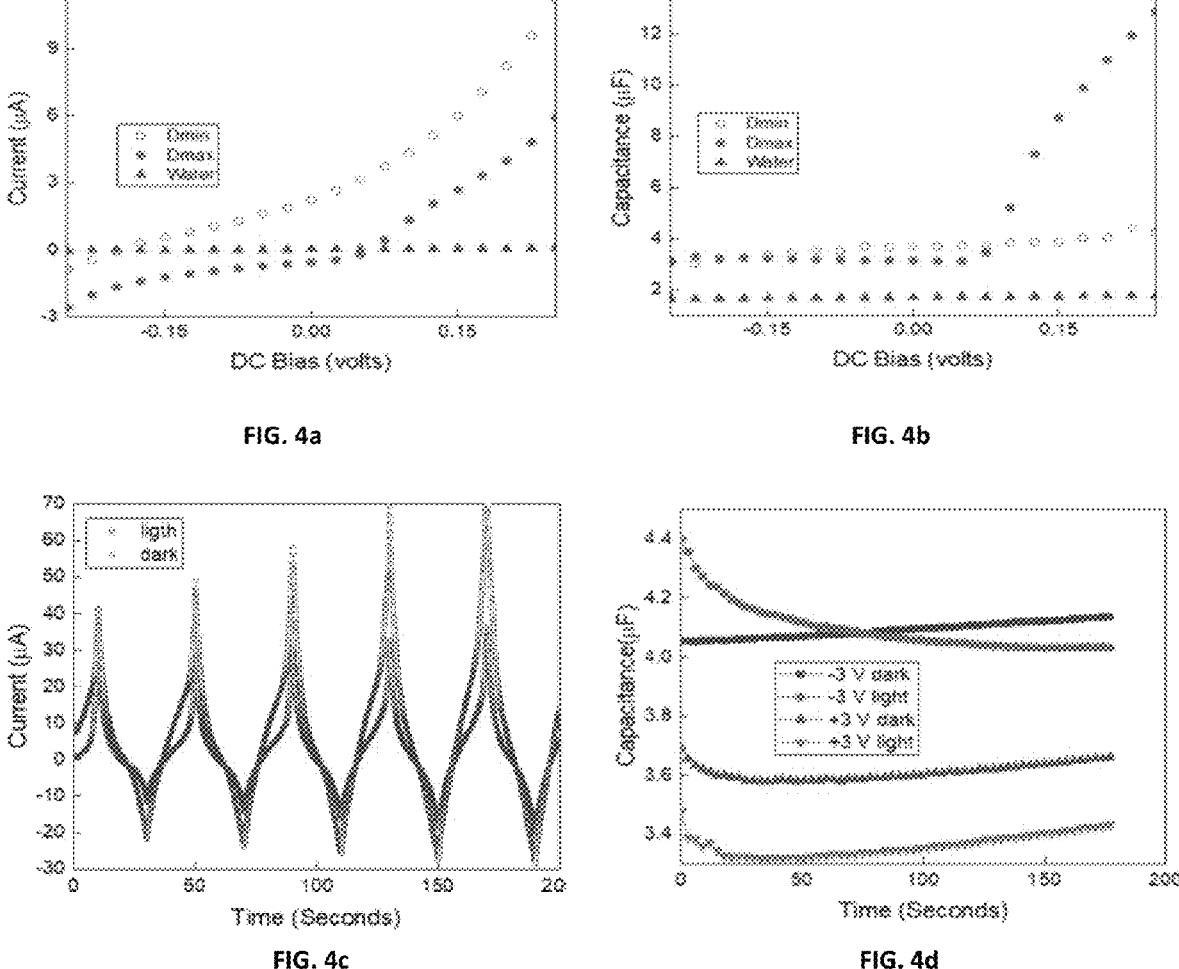
FIGS. 4a-4d shows graphs providing the characterization for DM melanin suspension.

FIGS. 4a-4d show the results of other current measurements. The IV characterization result is shown in FIG. 4a. Both curves ($D_{min}$ and $D_{max}$) show the Ohm's law IV dependence. This is also evident from the flat line of the control (pure water) measurement. For the same applied voltage value, however, the $d_{min}$ dilution exhibits a higher generated current. The capacitance-voltage profiles for the two dilutions along with the control are shown in FIG. 4b. The $d_{min}$ dilution shows a near flat slope in the change in capacitance with voltage. The $d_{max}$ dilution shows a flat response until a threshold voltage of about 80 mV then the capacitance rises dramatically with voltage. The current verses time plots extracted from the cyclic voltammogram (FIGS. 3a and 3b), are shown in FIG. 4(c). It is noted that the dry DM exhibited current measurements in the order of nanoamperes (FIG. 2b), whereas the current recorded using the DM in suspension is in the microampere range. Also, similar to the results with the dry DM melanin, the dark cycle plots show higher current amplitudes with a maximum of 81 μA while the light cycles show lower amplitudes with a maximum of 39 μA. The capacitance-time plots for one dilution is shown in FIG. 4(d), for dark and light cycling conducted at a frequency of 10 Hz. The two measurements were done at two voltages −0.3 V and 0.3 V.

In general, at the lower applied voltage higher capacitance is registered while at the higher applied voltage a lower capacitance is generated. It is also noted that the dark cycling generally showed relatively higher capacitance for both applied voltages. As the components of the date fruit melanin is not clearly identified, it is worth to mention that it may be coexisting with epi-catechin-based proanthocyanidins.

8

Results from Comparison Between DM Melanin Suspension and SM Melanin Suspension

Figure 5A:
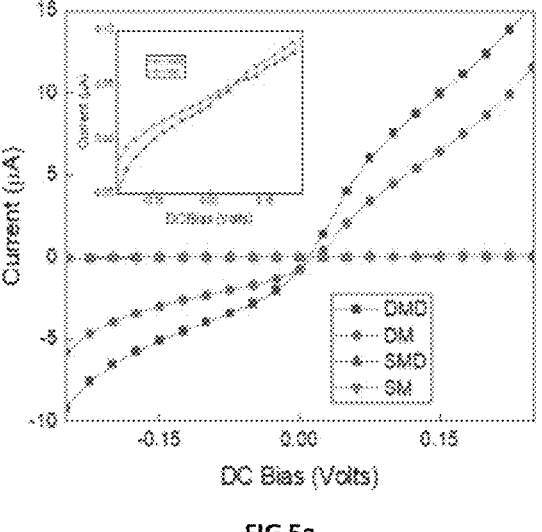
FIGS. 5a-5b shows IV measurements for DM and SM suspended in water.

Samples of DM and SM melanin were prepared to the same dilution and current-voltage measurements were performed in dark and light conditions with a 10 Hz low frequency applied. The results are shown in FIG. 5a. The SM does not exhibit any significant current flow for both the dark and light conditions as compared to the DM. The inset figure is a zoomed in plot. The light SM measurements show higher current than the dark ones. On the other hand, the DM very evidently demonstrates the Ohms law IV dependence. For the DM, below zero volt the light conditions show a higher current, however above zero volts the measurements in the dark environment exhibit a higher current.

Figure 5B:
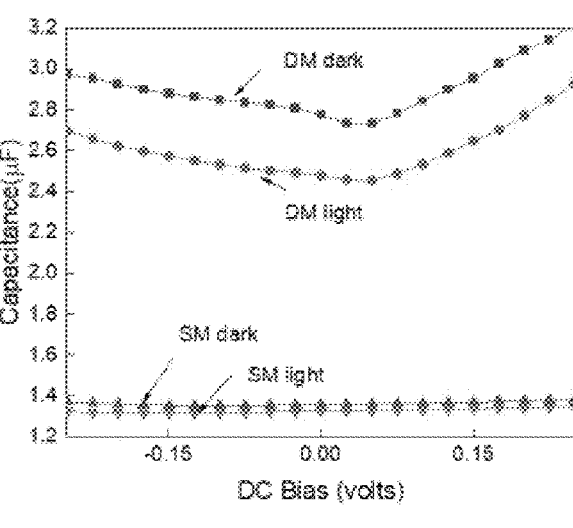

In FIG. 5b, the capacitance-voltage plots for the DM suspension and SM melanin measured in dark and light conditions are shown. For both types of melanin, the measurements in the dark showed higher capacitance than those done in the light. The SM however, in general showed lower capacitance (below 1.5 μF). Also, the capacitance remained constant with change in voltage. For the case of the DM however, there was a slight drop in capacitance at about 50 mV. Over the measurement range, the measurements in the dark conditions for the DM melanin were consistently higher by about 0.3 μF, as compared to the measurements done in the light.

Figure 6A:
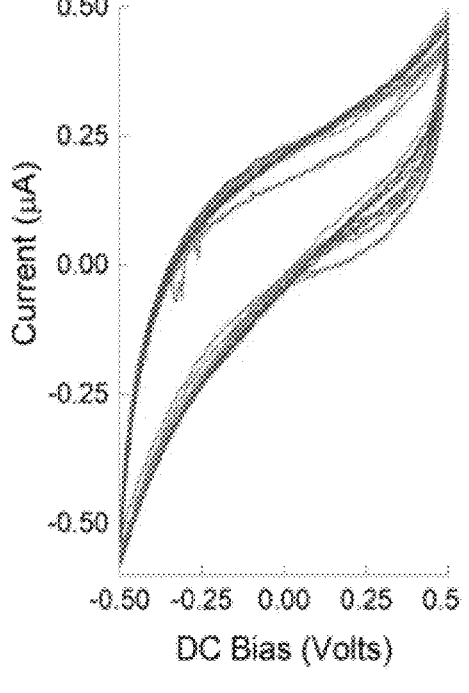
FIG. 6a shows cyclic voltammetry for SM melanin suspension for dark conditions.
Figure 6B:
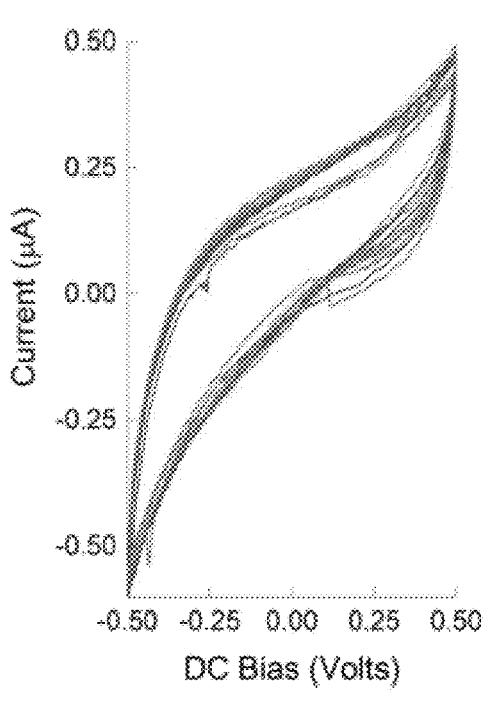
FIG. 6b shows cyclic voltammetry for SM melanin suspension for light conditions.

The results for the Cyclic voltammetry for SM suspension are shown in FIG. 6. There is not much difference in the plots for the dark and light measurements. However, the peak anodic and cathodic currents are over one order of magnitude than those recorded for the DM under the same measurement conditions.

Figures 7A, 7B, 7C, 7D:
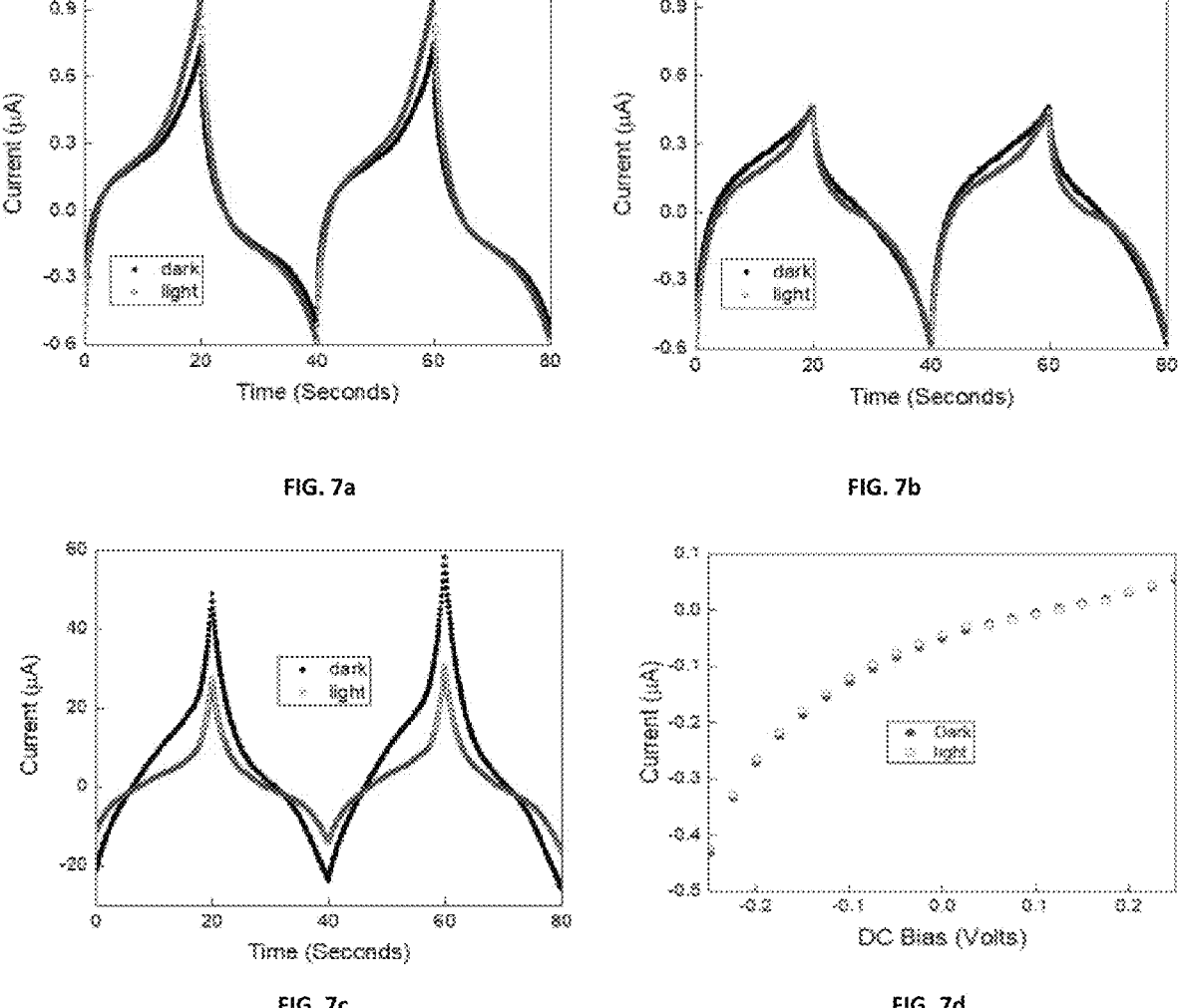
FIG. 7a shows graphs providing Light and dark result for current-time measurements extracted from Cyclic Voltammetry done on water.
FIG. 7b shows graphs providing current-time measurements for SM melanin suspension for $d_{max}$ dilution extracted from Cyclic Voltammetry.
FIG. 7c shows graphs providing current-time measurements for DM melanin suspension for $d_{max}$ dilution extracted from Cyclic Voltammetry
FIG. 7d shows graphs providing IV measurements for DM In DSMO.

The current verses time plots were extracted from Cyclic Voltammetry measurements and are shown in FIGS. 7a-7d. FIG. 7a shows the plots for measurements done on water as a control. The current-time measurement for SM and DM suspensions at $d_{max}$ dilution are shown in FIG. 7b and FIG. 7c respectively, for dark and light cycling. The most conspicuous difference between the two is the difference in the magnitude of the current peaks. The peak current for the SM is at about 490 nA, which is lower than the current values registered for the control experiment with water. On the other hand, the current peaks shown by the DM suspension are significantly higher, above over one magnitude higher (over sixty times higher), indicating a more sensitive photoconductive behaviour. A second observation is that the dark and light cycles have similar peak current for the SM suspension, while the dark cycles have higher peak current than the light for the DM suspension. This can be explained from the electronic theory. It is well known that the voltage is proportional to the product of current and resistance. For both the light and dark cycles, the voltage is varied across the same range, however the measurements result in different current readings. This implies that the suspension in light and dark conditions exhibits two different resistances. In the dark conditions, the resistance is lower hence higher current flow while in the light the resistance is higher hence lower current flow. The resistance behaviour is contrary to the conventional photosensitive behaviour. It is postulated that the resistance behaviour is due to the fact that when the melanin is diluted, it results in chemical self-doping that give its is ionic-electronic behaviour. When the suspension is further illuminated, the incident photons transfer energy to bound electrons creating even more free electrons. Since electrons inherently repel each other, this interaction between the abundance of electrons limits the current flow. In FIG. 7(d), the IV plot for DM diluted in Dimethyl sulfoxide (DMSO) at dilution $d_{max}$ is illustrated for measurements done in dark and light conditions. The two curves show similar performance. The current recorded however is significantly lower than that measured when the DM was diluted in water. It can be inferred that the DM has better conductivity in water.

Parameter Extraction for Characterization

To extract the electrical characteristics, IV data from measurements taken at 1 Hz (FIG. 2a: IV dry DM, FIG. 4a: IV water and DM at two dilutions) and 10 Hz (FIG. 5a: IV SM and DM in dark and light conditions) and CV data from measurements taken at 1 Hz (FIG. 2a: CV dry DM, FIG. 4b: CV water and DM at two dilutions) and 10 Hz (FIG. 5b: CV SM and DM in dark and light conditions) are used. For all experiments the voltages were varied between –250 mV and 250 mV. The ideality, conductivity, Debye length, doping, mobility, leakage current and permittivity were extracted using equations (1) to (7).

The results of the parameters extracted using equations (1) to (7) are shown in Table 1, for measurements done at 1 Hz. All the values except concentration are normalized to that of water.

TABLE 1

Semiconductor parameters extracted for melanin at 1 Hz for different concentrations of DM respectively.

| Param | Description | Dry DM melanin | DM melanin suspension (dmin) | DM melanin suspension (dmax) |
|---|---|---|---|---|
| $\rho$ | Concentration | Not applicable | 0.3 mg/mL | 30 mg/mL |
| n | Ideality | 0.9225 | 1.6569 | 1.1880 |
| $\sigma$ | Conductivity | 0.14 | 119.86 | 47.16 |
| $L_D$ | Debye length | 9.87E7 | 1.96 | 3.45 |
| N | Doping | 0 | 0.56 | 0.16 |
| M | Mobility | 0.15 | 72.39 | 39.72 |
| $I_0$ | Leakage current | 0.03 | 85.01 | −6.98 |
| $\varepsilon_s$ | Material permittivity | Not applicable* | 172.20 | 147.56 |

*It should be prepared as pellet in solid form to get rid of air to get a result.

The ideality factor describes how closely the IV characteristics approach that of an ideal diode. It can also describe showing a higher value. The two conductivity values for the two dilutions of DM melanin correspond to the values of the doping concentration calculated. The lower dilution DM ($D_{min}$) has a higher doping concentration and therefore higher conductivity as well as mobility, whereas the melanin with a higher dilution ($D_{max}$), has lower values.

The Debye length describes the net electrostatic effect of charge carriers in a solution. As the dilution of the melanin increases (from dry to maximum dilution) the calculated values of the Debye length increases. This can be explained by the fact that Debye length is proportional to the inverse of ion concentration. As expected, the dry DM melanin has a lower leakage current than the diluted melanin. Interestingly though, the direction of the leakage current for the heavily diluted melanin is reverse because of the increment in the corresponding Debye length. In terms of magnitude however, it is lower than the less diluted DM melanin suspension.

The dry DM melanin has the lowest relative permittivity for the three types of melanin. This is attributed to the fact that the experiments were conducted on powdered melanin. This implies that the existence of air between melanin particles would have the effect lowering of the effective dielectric constant significantly. It is known that a dielectric constant for dry melanin is the order of 101. However, this value was obtained for measurements done on melanin compressed into pellets. On comparing the permittivity of the melanin solutions, it was also noted that the permittivity of the more concentrated melanin was higher than that of the less concentrated melanin. The melanin solutions have higher relative permittivity than water. This implies that the DM suspension has a higher capacity for charge storage as compared to water.

For measurements done at 10 Hz, the results of the parameters extracted using equations (1) to (7) are shown in Table 2. All the values except concentration are normalized to that of water.

TABLE 2

Semiconductor parameters extracted for melanin at 10 Hz.

| Param | Description | SM melanin suspension (dmax) | SM melanin suspension (dmax) -dark | DM melanin suspension (dmax) | DM melanin suspension (dmax)-dark |
|---|---|---|---|---|---|
| $\rho$ | Concentration | 30 mg/mL | 30 mg/mL | 30 mg/mL | 30 mg/mL |
| n | Ideality | 1.002 | 1.0380 | 1.5371 | 1.6382 |
| $\sigma$ | Conductivity | 1.88 | 1.42 | 145.41 | 252.43 |
| $L_D$ | Debye length | 0.70 | 0.72 | 2.34 | 2.28 |
| N | Doping | 1.59 | 1.56 | 16.81 | 0.32 |
| $\mu$ | Mobility | 1.88 | 0.08 | 94.67 | 154.21 |
| $I_0$ | Leakage current | 1.39 | 1.75 | 33.10 | 77.02 |
| $\varepsilon_s$ | Material permittivity | 62.24 | 63.84 | 7330.98 | 132.20 | the type of carrier recombination processes occurring. Using water as a reference, the dry DM melanin has a lower ideality factor as compared to the diluted DM. The DM least diluted ($D_{min}$) shows a higher ideality factor than that with maximum dilution ($D_{max}$).

The electrical conductivity is an indicator of electron flow in a material. The dry DM melanin has a significantly lower conductivity (almost 3 orders of magnitude lower) than the diluted DM. The two diluted DM states ($D_{min}$ and $D_{max}$) have two different conductivities, with the lower dilution A comparison between the two types of melanin (SM and DM) shows that the SM has lower values of ideality, conductivity, Debye length, mobility, leakage current and material permittivity as compared to DM. This indicates that DM melanin with the same hydration state and under the same measurement conditions releases more charge carriers and therefore exhibits higher conductivity and charge storage capabilities. For the doping concentration however, the DM melanin shows significant variation between the measurements done in light and dark conditions as compared to the SM melanin. This implies that DM has a more sensitive photoconductivity behaviour.

One reason behind the difference in performance of SM and DM may be attributed to their classification. SM is part of the eumelanin category which in general have tyrosine, 5,6-dihydroxyindoles, as the monomer precursor. The DM falls in the category of allomelanins and its phenolic precursors may include epicatechin since the DM gives distinctive color after staining with 4-dimethylamino cinnamaldehyde (DMACA). The DM is not yet chemically characterized and it may also contain other constituents, e.g. parts of the fruit lignin and/or proanthocyanidins. The two types of melanin are therefore structurally different and this difference impacts the properties of conductivity, underwater adhesion, visible light absorption, free radical behavior and reducing/antioxidants properties.

The melanin's photostability depends on experimental conditions such as type of melanin, degree of hydration, pH, light intensity, oxygen concentration, and super-molecular structure. As most of the aforementioned factors were kept the same for the experiments with both types of melanin, it can therefore be concluded that the difference in results can be attributed to the factors that differed, that is, type of melanin and its super-molecular structure.

Considering the changes in performance between measurements done in light and dark conditions, only the ideality, mobility and leakage current values showed similar trends in both SM and DM melanin with the values calculated in the dark conditions being higher than those calculated in light conditions. The higher values obtained in dark values can be explained by the photoconductivity and heating induced water desorption behavior of melanin. When illuminated, a photocurrent is induced and non-radiative coupling occurs between the melanin and light. This coupling produces heat that reduces the water content of the melanin. As the melanin concentration increases, the resistance similarly increases. Due to the binding capacity of water for melanin, this effect is more noticeable for higher water content values than for lower ones. Hence, under light conditions a lower photoconductivity and therefore lower leakage current, ideality, and mobility values than under dark conditions. For the other parameters, the trend in SM was reversed in DM, for instance conductivity measured in light conditions was higher than that measured in dark conditions for SM, but the reverse was observed for DM.

Applications for Date Fruit Derived Melanin

Basing on the results of the characterization, the DM can find function in a number of applications owing to its redox reactions, biocompatibility and hydration-dependent hybrid electronic-ionic conduction that is attained through self-doping.

Example 1

Table 1 and table 2 provides that for measurements taken at 1 Hz or 10 Hz frequency, DM possesses high ideality, high conductivity, increased Debye length, high doping characteristics, high mobility.

Owning to these characteristics DM finds its use as an electrically conductive portion of an electronic component in an electronic device.

The electronic device may be any device requiring an electrically conductive portion with high charge storage capabilities. DM may be used in connection with the electrodes. DM may be used as a thin layer in connection with the electrodes or may be deposited on the electrodes to name a few.

Non limiting examples of devices that DM may find it usage in includes sensors such as humidity and PH sensors; solar (photovoltaic) cells, batteries, bioelectronic components including implantable devices owing to their biocompatible nature.

Example 2

Figure 8A:
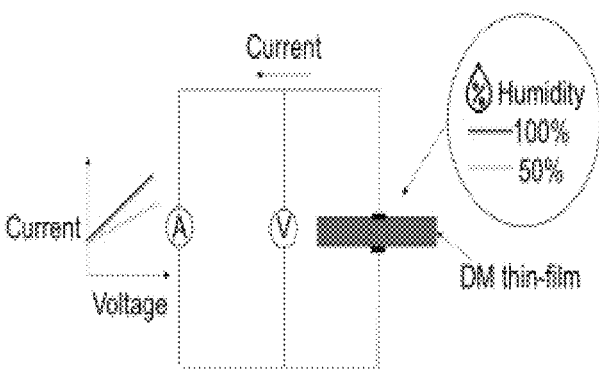
FIG. 8a shows an example of use of DM in humidity sensing in accordance with the invention.
Figure 8B:
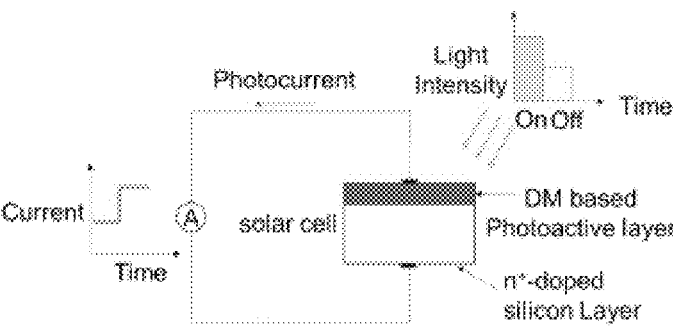
FIG. 8b shows an example of use of DM as a photoactive layer in a solar cell in accordance with the invention.

An example of an application of DM is in humidity sensing, as illustrated in FIG. 8a. The electrical conductivity of the DM depends on its concentration. This property can be exploited for use in relative humidity sensing.

FIG. 8a illustrates a simple electric circuit that can be used for humidity sensing and measuring. As illustrated in FIG. 8(a), thin films of DM are placed in connection with the electrodes. The electrodes may be any conductive material. In an embodiment, one or more gold electrodes are used in connection with DM. A voltage when applied across the electrodes, a resultant current is generated. The amount of current generated in the circuit is dependent on the relative humidity of the environment. At a higher humidity, the DM will absorb the moisture from the environment thereby increasing the dilution of DM.

The increase in the dilution of DM will result in an increase in the amount of self-doping, which would in turn result in larger current flow in the circuit.

Example 3

In another embodiment for humidity sensing and measuring, the method comprises generating a library of results for humidity measurement. This library will contain a list indicating the current generated at different levels of humidity. The same humidity sensor device may be used to generate a library of the current v/s humidity readings.

To generate the library reading, the humidity of the environment is maintained at a predetermined level. At that predetermined, a current reading is obtained. This reading is obtained by applying a voltage across the electrodes of the humidity sensor device. Similar current readings are taken at different humidity levels to generate a library.

To determine the current humidity level, on obtaining a current reading using the humidity sensor device provided in Example 2, the current reading is read against the library. The humidity measurement corresponding to the current reading obtained is the current humidity level of the environment.

Example 4

Another example of an application of DM is in solar cells, as illustrated in FIG. 8a. The power efficiency of a solar cell is impacted by the ability of the photoactive layer to absorb photons. As provided in table 2, DM showed significant variation between the measurements done in light and dark conditions. This implies a sensitive photoconductivity behaviour which enables its use in solar cells.

In an embodiment, a thin film heterojunction is formed by adhering a thin layer of melanin to an inorganic material, for example, silicon. To achieve a high photovoltaic performance, the band alignment between the two layers should be optimal, that is, the lowest unoccupied molecular orbital of the electron donor must be higher than the conduction band of the acceptor, and the highest occupied molecular orbital of the donor must be higher than the valence band edge of the acceptor. In this case, DM acts as the donor and the silicon the acceptor.

Also, to attain a good electronic contact, there should be good adhesion between the layers. On each of the layers, contacts are formed for the collection of holes and electrons. Depending on the solar cell illumination conditions, charge carriers are generated, and a photocurrent flows in the circuit. The high availability, low cost and broadband UV-Vis-NIR absorption spectra of melanin makes it a viable alternative for solar cell application.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

Certain features of the present invention are described in terms of a set of numerical upper limits and a set of numerical lower limits. It should be appreciated that ranges from any lower limit to any upper limit are within the scope of the invention unless otherwise indicated.

What is claimed is:

1. An electronic component comprising an electrically conductive portion, the electrically conductive portion comprising one or more electrodes and a date fruit derived melanin polymer, wherein the date fruit derived melanin polymer is in connection with the one or more electrodes and exhibits a higher electrical conductivity—in the absence of incident illumination than under incident illumination, wherein the incident illumination is provided by a light source emitting within an ultraviolet-visible spectrum and wherein the electrical conductivity is measured for a date fruit derived polymer at above zero volts at 10 Hz using a current-voltage measurement method; and wherein the date fruit derived melanin polymer is derived from a method comprising:
  providing a date fruit puree; and
  alkaline extraction of crude melanin.

2. The electronic component of claim 1, wherein the date fruit derived melanin polymer is a dry polymer or is an aqueous or gel suspension of the polymer.

3. The electronic component of claim 1, wherein a conductivity of date fruit derived melanin polymer ranges from about 0.14 siemens per meter to 119.86 siemens per meter, measured at 1 Hz using current-voltage measurement method.

4. The electronic component of claim 1, wherein an electron mobility of date fruit derived melanin polymer ranges from 0.15 to about 72.39, measured at 1 Hz using current-voltage measurement method.

5. The electronic component of claim 1, wherein a material permittivity of date fruit derived melanin polymer ranges from about 132 to 7330, measured at 1 Hz using current-voltage measurement method.

6. The electronic component of claim 1, wherein the electrical component forms part of an electronic device comprises any one of: a sensor, a photovoltaic cell, and/or bioelectronic component.

7. The electronic component of claim 1 is part of a humidity sensor device.

8. The electronic component of claim 1 is part of a photovoltaic cell.

9. The electronic component of claim 1 wherein the date fruit derived melanin polymer is in connection with an inorganic material.

10. The electronic component of claim 1 wherein the one or more electrodes comprise gold.

11. A method of forming an electrical component comprising an electrically conductive portion that comprises a date fruit derived melanin polymer, wherein the method comprises:

extracting date fruit derived melanin polymer according to a method comprising:
  providing a date fruit puree; and
  alkaline extraction of crude melanin;
forming the electrically conductive portion by incorporating the date fruit derived melanin polymer such that it is in connection with one or more electrodes, wherein the date fruit derived melanin polymer exhibits a higher electrical conductivity in the absence of incident illumination than under incident illumination, wherein the incident illumination is provided by a light source emitting within an ultraviolet-visible spectrum and wherein the electrical conductivity is measured for a date fruit derived polymer at above zero volts at 10 Hz using a current-voltage measurement method.

* * * * *